United States Patent
Leppäluoto et al.

(10) Patent No.: US 6,190,921 B1
(45) Date of Patent: Feb. 20, 2001

(54) OUABAIN IMMUNOASSAY AND KIT AND OUABAIN LABELED WITH $^{125}$I OR FLUORESCENT LABEL

(76) Inventors: Pekka Juhani Leppäluoto, Rantakatu 10 A 6, FIN-90100 Oulu; Lauri Erkki Olli Vakkuri, Niskalenkki 24, FIN-90650 Oulu; Olli Jaakko Vuolteenaho, Kelokuusenrie 8, FIN-90240 Oulu, all of (FI)

(*) Notice: Under 35 U.S.C. 154(b), the term of this patent shall be extended for 0 days.

(21) Appl. No.: 09/171,797
(22) PCT Filed: Feb. 25, 1998
(86) PCT No.: PCT/FI98/00167
§ 371 Date: Jan. 20, 1999
§ 102(e) Date: Jan. 20, 1999
(87) PCT Pub. No.: WO98/38511
PCT Pub. Date: Sep. 3, 1998

(30) Foreign Application Priority Data

Feb. 26, 1997 (FI) ..................................... 970801

(51) Int. Cl.$^7$ .................. G01N 33/534; G01N 33/53; G01N 33/555; G01N 33/567; C12Q 1/00
(52) U.S. Cl. .................. 436/172; 436/93; 436/519; 436/815; 436/822; 436/501; 436/836; 436/811; 436/817; 436/526; 436/518; 436/524; 436/537; 435/7.21; 435/7.24; 435/7.9; 435/7.92; 435/7.93; 435/7.25; 435/4; 435/5; 435/7; 435/7.1; 435/7.2; 435/7.94; 435/7.95; 530/388.24; 530/388.25; 530/389.2; 530/389.3; 530/389.8; 530/388.9; 536/24.31
(58) Field of Search .................. 435/7.24, 7.9, 435/7.93, 7.25, 4, 5, 7, 7.2, 7.1, 7.21, 7.94, 7.95; 436/93, 519, 815, 822, 501, 536, 811, 817, 526, 518, 524, 537; 195/63, 68, 99, 103.5, 103.7; 530/388.24, 388.25, 389.2, 389.3, 389.8, 388.9, 413, 412; 536/24.31, 25.4

(56) References Cited

U.S. PATENT DOCUMENTS 3,959,077 * 5/1976 Brooker .................................. 195/63
5,164,296 * 11/1992 Blaustein et al. ................... 435/7.24

(List continued on next page.)

FOREIGN PATENT DOCUMENTS 0 106 370 A3    4/1984    (EP).
0 184 630 A3    6/1986    (EP).

(List continued on next page.)

OTHER PUBLICATIONS

Chatterjee et al., "Iodoacetylated ouabagenins: their syntheses, spectroscopic characterizations, and stability studies, Steroids"; vol. 60, pp. 477–483, 1995.*

Harwood et al., "Development of enzyme immunoassay for endogenous ouabain–like compound in human plasma". Clinical Chemistry, vol. 43, No. 5, pp. 715–722, 1997.*

Paci et al. "Commercial enzyme immunoassay reagent pack for ouabain compared with human placenta radioreceptor assay". Clinical Chemistry, vol. 42, No. 4, pp. 648–650, 1996.*

(List continued on next page.)

*Primary Examiner*—Long V. Le
*Assistant Examiner*—Lisa V. Cook
(74) *Attorney, Agent, or Firm*—Nath & Associates PLLC; Gary M. Nath; Joshua B. Goldberg

(57) ABSTRACT

The invention deals with the use of a reactive compound in immunological analyses. The compound is ouabain or its analog to which another compound, labeled by radioiodine or by a fluorogen, is coupled. The invention covers also the method to measure ouabain or its analog in plasma to diagnose cardiovascular and endocrine diseases and other harmful conditions.

4 Claims, 2 Drawing Sheets

U.S. PATENT DOCUMENTS

Figure 1:
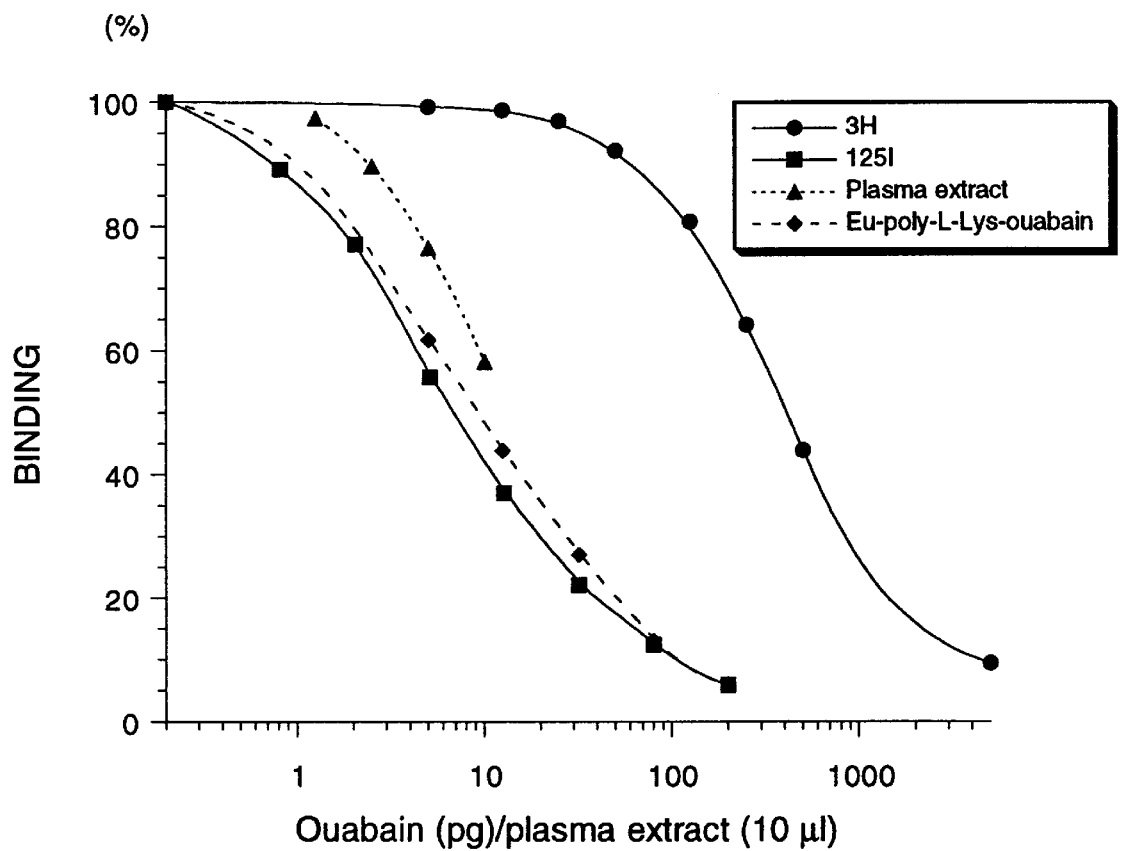

| | | | |
|---|---|---|---|
| 5,429,928 | * | 7/1995 | Blaustein et al. .................... 435/7.24 |
| 5,705,402 | * | 1/1998 | Leland et al. ......................... 436/528 |
| 5,770,376 | * | 6/1998 | Bagrov .................................. 435/7.1 |

FOREIGN PATENT DOCUMENTS

| | | | |
|---|---|---|---|
| 0 218 010 A3 | | 4/1987 | (EP) . |
| 0 489 393 A3 | | 6/1992 | (EP) . |
| 0106370 A2 | * | 4/1984 | (US) .............................. G01N/33/54 |
| 0186630 A2 | * | 6/1986 | (US) .............................. G01N/33/94 |
| 0489393 A2 | * | 6/1992 | (US) ............................ G01N/33/534 |

OTHER PUBLICATIONS

Gottlieb et al., "Elevated concentrations of endogenous ouabain in patients with congestive heart failure", Circulation, vol. 86, No. 2, pp. 420–425, 1992.*

Selden et al., "Ouabain pharmacokinetics in dog and man", Circulation, vol. 45, No. 6, pp. 1176–1182, 1972.*

Mita Chatterjee et al.; Iodoacetylated ouabagenins: Their synthesis, spectroscopic characterizations, and stability studies; Steroids 60: 477–483, 1995.

* cited by examiner

OUABAIN IMMUNOASSAY AND KIT AND OUABAIN LABELED WITH $^{125}$I OR FLUORESCENT LABEL

This application is based on International Application Serial No. PCT/FI98/00167, filed Feb. 25, 1998, which claims priority to Finland Application Serial No. FI 970801, filed Feb. 26, 1997.

The present invention deals with the use of a reactive compound in immunological analyses as a tracer, which compound comprises ouabain or an analog thereof attached to a compound labeled by a detectable radioiodine or fluorogen. The invention covers also the methods in which the reactive compounds are used in the measurements of the concentrations of ouabain, ouabain isomers, ouabagenin or ouabagenin isomers in biological fluids, especially in plasma for the diagnoses of cardiovascular and endocrine diseases and other harmful conditions.

Sodium-potassium-adenosine triphosphatase (Na—K—ATPase) is a cell membrane enzyme, the main function of which is to transport the sodium ion to the extracellular space. Since it is known that cardiac glycosides inhibit Na—K—ATPase (Goto et al., Pharmacol. Rev. 44;377–399, 1992), it has been assumed that the compounds resembling glycosides act as physiological natriuretic hormones. The search for natriuretic hormones has led to the purification and chemical characterization of a cardiac glycoside ouabain from human plasma (Hamlyn et al Hypertension 10, [Suppl I]; I-71–I-77, 1987; Hamlyn et al. Proc. Natl. Acad. Sci. USA 88:6259–6263, 1991; Ludens et al., Hypertension 17:923–929, 1991). Ouabain or a structurally closely resembling compound has also been isolated from the mammalian adrenal cortex (Shaikh et al. J. Biol. Chem. 266: 13672–13678, 1991) and from hypothalamus (Alaghband et al., J. Endocrinol. 98:21–226,1983). High levels of ouabain have been found in the adrenals, and adrenalectomy or changes in the intake of electrolytes lead to changes in plasma ouabain levels (Ludens et al., Hypertension 19:721–724,1992; Hamilton et al., Current Opinion in Endocrin. and Diabetes 1:123–131, 1994; Laredo et al., Endocrin. 153:794–797, 1994). However. the measurement methods used in the above mentioned studies have not been reliable. Ouabain isolated from human plasma or bovine hypothalamus may differ slightly from plant-derived ouabain, although they have similar characteristics in liquid chromatography and mass spectroscopy (Zhao et al., Biochemistry 34:9893–9896, 1995).

Plant-derived ouabain has been used as a drug named G-strophantin for the treatment of heart failure. Since there is ouabain also in the human body, it was assumed that the secretion of ouabain could be elevated in cardiovascular diseases, for example. Now it is clear that the plasma levels of ouabain are very low and their reliable measurement is problematic. It is possible to reach the necessary sensitivity with radioimmunological analyses, but high sensitivity leads to unspecific reactions. The first radioimmunoassay of ouabain was published in 1986 (Masugi et al., Biochem. Biophys. Res. Commun. 135:41–45, 1986). The method used a polyclonal antiserum and tritiated ouabain as the tracer. Later several researchers have developed immunoanalyses for the measurements of ouabain in body fluids (Hamlyn et al. Proc Natl Acad.Sci.USA 88;6259–6263; Naruse et al., Hypertension 23, [Suppl I]; I-102–I-105, 1994; Harris et al., Hypertension 17:936–943,1991) However, the plasma ouabain levels reported have varied considerably, from below 5 (Lewis et al., Hypertension 24:549–555, 1994) to 440–530 pmol/l (Gottlieb et al., Circulation 96:420–425, 1992; Rossi et al., J. Hypertension 13(10):1181–1191, 1995), when the samples are extracted by a solid phase system. The high variability shows clearly that there is a need for a sensitive and reliable measurement method of ouabain for clinical and physiological studies and for diagnostic purposes.

Zhao et al., (Biochemistry 34:9993–9896,1995, recently showed that naphtolyated ouabain-like compounds isolated from human plasma or from bovine hypothalamus differ from autenthic ouabain in a reverse phase HPLC. The naphtolyated compounds had a different CD spectrum from naphtolyated authentic ouabain. They concluded that the previously isolated compound is a new isomer of the plant-derived ouabain, in which there is a different attachment for hydroxyl groups and/or a different stereochemistry in the steroid moiety. It is notable that the native isomer does not differ from the plant-derived ouabain in mass spectroscopy or in chromatographical and immunological characteristics, whereby immunoanalysis of ouabain can be used for measurement of an endogenic compound.

When ouabain was isolated as a candidate for an endogenous natriuretic hormone, plasma levels of ouabain were measured by an ELISA method (Hamlyn et al., reference above). By using this method human plasma samples extracted by a resin were found to contain 138 pmol/l of ouabain immunoreactivity. Later even higher plasma ouabain levels have been reported, but the nature of the immunoreactivity was not studied (Gottlieb et al., Rossi et al. references above). The immunoreactive material extracted from large plasma volumes behaved identically with the authentic ouabain in two different reverse phase HPLC systems (Harris et al., reference above). Four other subsequent studies were however not able to confirm this result The presence of ouabain could not be shown when plasma samples were extracted by solid phase methods and measured by two different ELISA methods with a sensitivity of 30–60 pmol/l (Gomez-Sanches et al., Am J. Hypertension 7:647– 650,1994) or by a radioimmunoassay with a sensitivity of 75 pmol/l (Doris et al. Hypertension 23(5):632–638, 1994). Nor did HPLC analyses with larger plasma volumes give any evidence for the presence of ouabain in human plasma (Lewis et al., Doris et al., see above). Very low plasma ouabain levels have also been documented, but the serial dilutions of plasma extracts were not comparable with those obtained with ouabain (Worgall et al. J Hypertension 14(5):623–629, 1996) and with HPLC analyses detectable amounts of immunoreactivity could not be shown when test eluated with authentic ouabain (Worgall et al., Gomez-Sanches et al., see above). Based on the facts presented above it appears clear that the low sensitivity of the immunoassays using tritiated ouabain or of the ELISA methods used so far is the main reason why the results of the above mentioned studies have led to the conclusion that there is no ouabain in human plasma.

The purpose of the present invention is to achieve a sensitive and reliable measurement method for plasma ouabain or for its analogs to be used in the immunoanalyses of ouabain in the diagnoses of e.g. diseases related to heart failure. This purpose has been fulfilled according to the invention by using polyclonal antisera of high affinity and radioiodinated or fluorogen labeled ouabain compounds of high specific activity and reverse phase separation with $C_{18}$ resins to achieve a very sensitive immunoanalysis, which can be used for routine measurements of endogenous ouabain or its analog.

The essential features of the invention have been presented in the enclosed patent In the course of the invention it was found, somewhat surprisingly, that the use of radioiodine, especially of $^{125}$I, or a fluorogen, especially of a lanthanide such as Europium instead of $^3H$ dramatically improves the sensitivity of the ouabain radioimmunoassay. Other isotopes of iodine such as $^{131}I$ can also be used, sine the isotopes are chemically similar. The ouabain compound labeled by $^{125}I$ or by Eu-chelate had clearly better sensitivity—about 100-fold higher than the previously used ELISA methods or radioimmunoassays using $^3H$ tracers. In place of the Eu chelate Samarium or Terbium chelates could be used, since their chelate residues are similar to that in the Eu chelate. The radioimmunoassay presented in the invention is able to detect ouabain levels of 0.5 fmol/assay tube. The previously described most sensitive methods detect 10–20 fmol/assay tube or well (Harris et al., see above). The method presented in the invention combined with $C_{18}$ reverse phase separation is able to detect as low an amount of immunoreactive ouabain as 10.8 pmol/L in healthy human plasma. The recovery of the solid phase separation is close to 100% and the dilutions of plasma extracts are comparable with those of authentic ouabain in the radioimmunoassay presented in the invention. In addition, the immunoreactivity of plasma exctracts eluted identically with authentic ouabain in two different reverse phase HPLC systems. This shows clearly that ouabain or a closely related compound occurs in human plasma, but at concentrations that are below the sensitivity limits of previously known immunoanalyses of ouabain.

The proposed invention shows that it is possible by the method presented in the invention using ouabain analog labeled by radioactive iodine or fluorogen and reverse phase separation to detect a compound from human plasma that is immunologically and chromatographically indistinguishable from authentic ouabain. The levels of ouabain detected by the method presented in the invention are considerably lower than those obtained by the earlier methods. High plasma levels can even be measured from au unextracted sample.

The following is a representation of the invention by figures.

In FIG. 1 the binding of different labels ($^3H$, $^{125}I$ and Eu) is expressed as percentages of the maximal binding as a function of the amounts of ouabain (picograms) or of the volume of extracted plasma (microliters). It is noted that when iodine-125 or Europium is used, the sensitivity is 100-fold higher than when using $^3H$. Serial dilutions of human plasma extracts also displace the label in the same way as ouabain diluted in a similar way.

Figure 2:
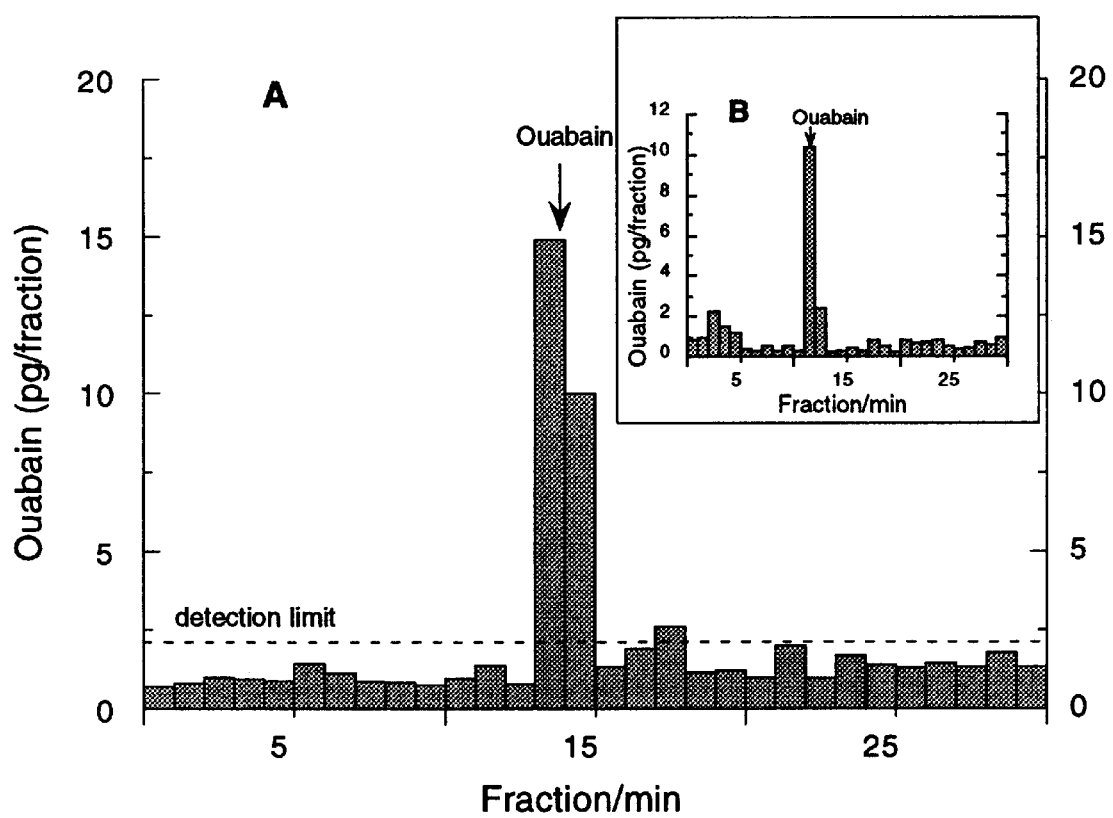

FIG. 2 depicts an analysis of human (A and B) plasma ouabain-like immunoreactivity in a reverse phase HPLC. 6–12 ml of plasma was purified in Sep-Pak extraction and the extract was analyzed in a Vydac $C_{18}$ column using an acetonitrile gradient from 0 to 40% in 0.1% trifluoroacetic acid for 30 min (A) or in a Vydac pH stabile $C_8$ column using an acetonitrile gradient from 5 to 50% in 0.1 M $NH_4HCO_3$ for 30 min (B). One third of the main immunoreactive compound of run A was transferred to the column used in B. Fractions of one milliliter were collected and analyzed for their ouabain-like immunoreactivity The arrow points to the elution of authentic ouabain.

The following describes the invention in derail by examples.

EXAMPLES

1. Materials

Ouabain (G-Strophantin) octahydrate, ouabagenin, digoxin, digitoxin and related steroids (aldosterone, cortisone, hydrocortisone, progesterone, beta-estradiol and testosterone), bovine thyroglobulin, poly-L-lysine and sodium cyanoborohydride were obtained from Sigma Chemical Company (St. Louis, Mo., USA). Freund's incomplete and complete adjuvant were purchased from Difco Laboratories (Detroit, Mich., USA), L-tyrosine and polyethylene glycol 6000 from Fluka AG (Buchs, Switzerland), $^3H$-ouabain (21,22 $^3H$-ouabain) and Na $^{125}I$ (IMS 300) from Amersham International plc (Buckinghamshire, U.K), Eu chelate from Wallac (Turku, Finland) and Sephadex G 50F from Pharmacia (Uppsala, Sweden). All the other chemicals were obtained from E. Merck AG (Darmstadt, Germany).

2. Preparation of ouabain antigen and antisera

Ouabain was coupled to bovine thyroglobulin using the method of Masugi et al. (Biochem. Biophysics Res. Comm. 135:41–45, 1986). The ouabain-thyroglobulin conjugate was purified in gel filtration (Sephadex G-50F in 0.9%/O NaCl) The conjugate was emulsified in Freund's complete adjuvant and injected subcutaneously to five rabbits (1 mg/rabbit). Booster injections (0.5 mg/rabbit in Freund's incomplete adjuvant) were given at monthly intervals.

3. Preparation of radioiodinated ouabain tracer

According to the invention ouabain was coupled first to L-thyrosine by the method which has previously been used to couple a protein (albumin, thyroglobulin) to ouabain. Ouabain (3.1 mg) reacted with $NaIO_4$ in distilled water (0.1 ml). Ethanol was added to the solution and pH was adjusted to 8 by NaOH. L-tyrosine (0.8 mg in 0.4 ml of 0.05M sodium phosphate, pH 9) was added dropwise and incubated for 2 hours. Sodium cyanoborohydride (0.25 mg in 0.2 ml of distilled water) was added and the reaction mixture was purified in reverse phase HPLC (Vydac $C_{18}$ column in 0.05% trifluoroacetic acid using a methanol gradient of 1%/min). The WV (220 nm) peaks obtained in HPLC were studied for their immunoreactivity and the peak eluting at 23.7 min was the thyrosylated ouabain analog, since it could be iodinated and since it was immunoreactive. The thyrosylated compound (1 µg) was radioiodinated by Na $^{125}I$ using Chloramine-T (5 µg). After 30 sec the reaction was stopped by sodium metabisulphite and the tracer was purified in reverse phase HPLC by using 12–60% acetonitrile gradient in 0.1% trifluoroacetic acid. The radioiodinated tracer was eluted at 22 min.

4. The preparation of the fluorogenic ouabain tracer

Analogically, according to Example 3 ouabain was first coupled to poly-L-lysine by sodium cyanoborohydride: after ouabain (2.9 mg) was reacted with $NaIO_4$ overnight at +4° C. in distilled water (0.7 ml) ethanol 0.7 ml was added and the pH of the solution was adjusted to 8 by NaOH. Thereafter poly-L-lysine (0.5 mg in 0.1 ml of 0.05 phosphate buffer, pH 9) was added to the reaction solution and after two hours sodium cyanoborohydride (0.25 mg in 0.1 ml of distilled water). The reaction mixture was fractionated in reverse phase HPLC (Vydac $C_{18}$ column in 0.05% trifluoroacetic acid) by using a methanol gradient (from 5 to 35%/min.). The immunoreactivity of the fractions in relation to UV absorption (220 nm) was tested in ouabain $^{125}I$-RIA. The peak having the highest immunoreactivity (and at the same time the highest UV) obtained in the afore-mentioned HPLC (fraction number 26) was ouabain-poly-L-lysine that was then chosen for $Eu^{3+}$ labeling. This amount of the fraction (about 12 µg in 0.25 ml of 0.1 M $NaHCO_3$, pH 9) was reacted with the Eu chelate (0.1 mg in 0.25 ml in 0.1 M $NaHCO_3$, pH 9) overnight at +4° C. The reaction solution was fractionated in reverse phase HPLC (Vydac $C_8$ pH stabile column in 0.05 M $NH_4HCO_3$ at pH 7.8 by using a methanol gradient from 5 to 35%). The fluorogenic fractions were tested for their ouabain immunoreactivity. In FIA (fluoroimmunoassay) the fraction eluting at 20 min gave the titer and the sensitivity that was comparable with the displacement curve in the RIA (see FIG. 1). As the figure shows, the sensitivity was about 100-fold higher than the curve set by the $^3$H tracer.

5. Radioimmunoassays

All five rabbits produced antiserum against ouabain conjugated to thyroglobulin after the primary immunization. After three booster injections the titers giving 30% binding were between 1:3,000 and 1:7,000 by using $^3$H ouabain tracer and between 1:300,000 and 1:1,000,000 by using $^{125}$I ouabain tracer.

Ouabain standards and samples used in assays were pipetted in 0.1 ml dublicates. The antiserum ("199", final dilution 1:1,000,000) and the ouabain tracer (Eu, $^{125}$I or $^3$H labeled) were added together in 100 ml. After an overnight incubation the bound and free fractions were separated by double antibody precipitation in the presence of 8% polyethylene glycol, and the precipitates were counted for radioactivity. When $^3$H-ouabain was used as a tracer, the precipitates were dissolved in scintillation fluid before counting in a beta-counter.

The sensitivity of ouabain radioimmunoassay with all antisera was below 1 pg/assay tube and the 50% displacement took place at 2–10 pg/assay tube when using Eu-labeled or radioiodinated ouabain analog as the tracer. The antiserum coded "199" was selected for further use. Its sensitivity was over 100-fold higher using radioiodinated compared with the $^3$H tracer (0.3 and 32 pg/tube or 0.5 and 57 fmol/tube, respectively, see FIG. 1). The within and between assay coefficients of variation were 3.8% and 3.7% at 10.8 pg/tube and 22.2 and 9.1 at 49.2 pg/tube, respectively (N=12).

The antiserum "199" detected the ouabain residue specifically. Of the compounds tested ouabagenin showed the highest cross-reactivity, 52%, as could be expected considering the method of the conjugation. Digoxin and digitoxin cross-reacted slightly (below 1.7%), whereas no detectable cross-reactivity (below 0.001%) was seen with naturally occurring steroids such as aldosterone, progesterone, testosterone or beta-estradiol.

6. Solid phase separation of plasma samples

Ouabain was extracted from 1–2 ml plasma samples with Sep Pak$^R$ Vac 500 mg $C_{18}$ cartridges (Waters, Milford Mass. USA) using an automated Gilson 5100 Aspec system. The cartridges were preconditioned with 2 ml of 2-propanol and 4 ml of 0.1% aqueous trifluoroacetic acid (TFA) and thereafter loaded with the plasma sample to which 0.2 ml of 1 M HCl and 1.6% glycine per ml was added. The cartridge was then washed with 0.1% trifluoroacetic acid (2 ml). Ouabain was eluted from the cartridge with 2 ml of 40%o acetonitrile in 0.1% TFA. The eluates were evaporated and dissolved to 0.25 ml of the buffer used in ouabain RIA.

7. HPLC analysis of the plasma extracts

SepPak plasma extracts (see above) were dissolved in 01% trifluoroacetic acid (TFA), centrifuged, filtered and subjected to reverse phase HPLC using a Vydac $C_{18}$ 218TP column (0.46×15 cm, Hesperia, Calif., USA). A 30-mm linear gradient from 0 to 30% acetonitrile in 0.1% TFA was run with a flow rate of 1 ml/min. Fractions of 1 ml were collected and dried in Speed Vac, reconstituted with 250–500 μl of RIA buffer and subjected to the ouabain radioimmunoassay. One third of the major immunoreactive peak of the chromatography was reanalyzed in a Vydac $C_8$ pH stable column (228TP, 0.46×25 cm) eluted with a 30-min linear gradient from 5 to 50% acetonitrile in 0.1 M $NH_4HCO_3$. The flow rate was 1 ml/min and 1 ml fractions were collected. Blank runs with pure aqueous buffer as a sample did not show any ouabain immunoreactivity. Recovery (Sep-pak) and calibration (HPLC) analyses were performed by adding ouabain (50 or 100 pg) to human plasma extracts before chromatography. The HPLC analyses were repeated three times.

8. Validation of the radioimmunoassay for use with human plasma samples

Reverse phase extraction with $C_{18}$ cartridges was used to concentrate and puff ouabain in plasma samples. The extraction recovery of ouabain added to 1 ml of human plasma was 102.8±2.5% at 25 pg and 93.6±1.3% at 75 pg (mean±SFM, n=5). Endogenous immunoreactivity in plasma extracts diluted parallelly with the ouabain standard (FIG. 1) and eluted identically with authentic ouabain in two reverse phase HPLC systems with different selectivities (FIG. 2). The recovery from HPLC of ouabain added to plasma exatet was 89.6%.

9. Patient samples

Blood samples from 20 pregnant women representing trimesters II–III and from 31 hypertensive patients (males and females, aged 45–82 years) treated with a -blocker, ACE inhibitor, diuretics and/or nitroprusside were taken into EDTA tubes. Plasma was separated and stored at –20° C. Blood samples from 22 laboratory workers (male and female, aged 25–56 years) were collected to serve as normal controls. All the samples were collected at 9–12 am.

10. Immunoreactive ouabain in human plasma

The plasma ouabain level in healthy females aged 22–45 years was 10.3±1.6 pmol/l (mean±SEM, n=10) and in males aged 23–56 years 11.4±1.2 pmol/l (n=12). The mean plasma ouabain level in pregnant patients (trimesters II and III) was 21.6±1.1 pmol/l (n=20), in other words significantly higher than in non-pregnant women. Hypertensive patients had generally lower plasma ouabain levels, 7.3±2.1 pmol/l (n±31), than the controls, but in two patients the plasma levels were clearly higher, 61 and 34 pmol/l. These patients had high levels of plasma BNP and N-terminal fragment of proANP as well, evidently showing increased cardiac volume and stretch. Because the sample had three other hypertensive patients with high plasma ANP, NT-proANP and/or BNP, but a normal ouabain level, our observation refers to the fact that patients with a high immunoreactive ouabain level in plasma, may have a hypertension of a new type.

Findings have been published recently of very high levels of immunoreactive ouabain in plasma of a patient who had a small cell cancer, ectopic ACTH syndrome and high blood pressure. This patient's blood pressure correlated with plasma immunoreactive ouabain, showing that the ouabain compound can cause high blood pressure (Goto et al., Hypertension 28:421–425, 1996). During pregnancy the immunoreactivity levels of ouabain were twice as high as normal. This can be caused by an increase of plasma volume during pregnancy. This finding might be in connection with previous research where an increase of Na-K-ATPase bioactivity was detected during pregnancy (Graves, Hypertension 10:84–86, 1987).

What is claimed is:

1. An immunologically reactive complex comprising three members, ouabain, a compound and an element, to be used as a tracer in ouabain immunoassays in which
   a) said compound coupled to ouabain is tyrosine or histidine or a peptide or protein containing tyrosine or histidine,
   b) said element attached to said compound is radioactive iodine, $^{125}$I, or lanthadine selected from the group consisting of Europium, Terbium or Samarium, or a group labeled by radioactive iodine, preferably $^{125}$I, or by lanthadine selected from the group consisting of Europium, Terbium or Samarium.

2. An immunoassay method in which the tracer as claimed in claim 1 is used for determination of ouabain in solid phase extracts of plasma to diagnose cardiovascular, endocrine or tumor-related diseases.

3. An immunoassay method of claim 2 comprising the following steps:
   a) a blood sample is taken from a subject and plasma is separated from the blood sample,
   b) ouabain is concentrated from the plasma sample,
   c) an ouabain-specific antibody is used together with a tracer as claimed in claim 1 and concentrated plasma samples or known amounts of ouabain, unbound tracer is removed and the level of bound tracer is measured, and
   d) the level of ouabain in step c) is compared with the standard to determine the level of ouabain in the plasma of the subject.

4. An immunoassay method of claim 2, the method being characterized by
   a) having a displacement curve with ouabain in immunoassays,
   b) having the lowest detectable level of ouabain of 0.5 fmol/assay tube,
   c) detecting the oubain immunoreactivity of plasma or serum similarly with ouabain in several reverse Phase high performance liquid chromatographies,
   d) showing complete recovery from plasma sample, and/or
   e) not showing detection below 0.001% cross reactivity with naturally occurring steroids, selected from the group consisting of aldosterone, progesterone, testosterone and estradiol.

* * * * *